(12) United States Patent
Keeney et al.

(10) Patent No.: US 8,476,193 B2
(45) Date of Patent: Jul. 2, 2013

(54) STABLE OIL-IN-WATER EMULSIONS

(75) Inventors: Franklin N. Keeney, Carmel, IN (US); Mei Li, Westfield, IN (US)

(73) Assignee: Dow AgroSciences, LLC., Indianapolis, IN (US)

( * ) Notice: Subject to any disclaimer, the term of this patent is extended or adjusted under 35 U.S.C. 154(b) by 0 days.

(21) Appl. No.: 12/897,174

(22) Filed: Oct. 4, 2010

(65) Prior Publication Data

US 2011/0082039 A1 Apr. 7, 2011

Related U.S. Application Data

(60) Provisional application No. 61/248,983, filed on Oct. 6, 2009.

(51) Int. Cl.
*A01N 25/32* (2006.01)
*A01N 25/00* (2006.01)
*A01N 43/42* (2006.01)

(52) U.S. Cl.
USPC ............... 504/105; 504/116.1; 504/247

(58) Field of Classification Search
None
See application file for complete search history.

(56) References Cited

U.S. PATENT DOCUMENTS

| 5,599,768 A | * | 2/1997 | Hermansky | 504/211 |
| 2008/0032890 A1 | | 2/2008 | Jensen et al. | |
| 2008/0058209 A1 | | 3/2008 | Jensen et al. | |

FOREIGN PATENT DOCUMENTS

| DE | 10 2006 056083 A1 | | 5/2008 |
| WO | WO 01/93679 A1 | | 12/2001 |
| WO | WO0236566 A1 | | 5/2002 |
| WO | WO 02/067682 A1 | | 9/2002 |
| WO | WO 2009/012979 A2 | | 1/2009 |
| WO | WO 2009/029518 A2 | | 3/2009 |
| WO | WO 2009/032481 A2 | | 3/2009 |
| WO | WO-2009032481 | * | 3/2009 |
| WO | PCT/US10/051282 | | 4/2010 |

* cited by examiner

*Primary Examiner* — Alton Pryor
(74) *Attorney, Agent, or Firm* — Robert Chang

(57) ABSTRACT

Interaction of cloquintocet mexyl in the discontinuous oil phase with water in the continuous aqueous phase of an oil-in-water emulsion, which can lead to cloquintocet mexyl hydrate formation, crystal formation and Ostwald ripening, is minimized by the use of specific surfactants and solvents which provide enhanced stability to the emulsion.

22 Claims, No Drawings

STABLE OIL-IN-WATER EMULSIONS

This application claims the benefit of U.S. Provisional Application Ser. No. 61/248,983 filed on 6 Oct. 2009.

FIELD OF THE INVENTION

This invention concerns novel oil-in-water emulsion compositions that prevent crystal formation and Ostwald ripening of cloquintocet mexyl hydrate.

BACKGROUND OF THE INVENTION

Agricultural formulation products must be physically and chemically stable for a specified period of time in order to have commercial utility. There are many causes of formulation instabilities, such as active ingredient instability, phase separations (Oswald ripening, crystallization, sedimentations, creamings, etc.) or environmental factors (temperature, humidity/moisture, etc.). In today's agrichemical market, it becomes increasingly common to develop new formulations to contain multiple active ingredients and their required solvents, safeners, and/or adjuvants, etc., in order to achieve the optimal spectrum, efficacy, and delivery efficiency, which consequently makes formulation stability more and more challenging. Therefore, technologies that can effectively isolate, hinder, or eliminate, adverse reactions or interactions between incompatible ingredients are often critical for a successful product.

Cloquintocet mexyl (CQC-M) is a quinoline compound that has the following chemical structure. It functions as an herbicide safener by reducing the phytotoxic

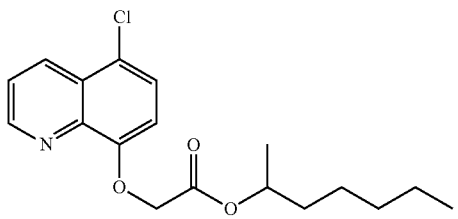 [SMILES: CCCCCC(C)OC(=O)COc1ccc(Cl)c2cccnc12]

effects of the herbicide on crops to which it is applied. The preparation and action of quinoline safeners has been disclosed in a series of publications such as DE 2546845, U.S. Pat. No. 3,351,525, Chem. Abstr. 79 (1973) 53154r and EP 94 349.

CQC-M will easily convert to its hydrate form upon contact with water as disclosed in WO 02/36566 A1. CQC-M hydrate will then proceed to precipitate as large needles that hinder sprayability and subsequently its ability to function as an herbicide safener. Because of this undesirable hydrate formation, CQC-M is normally formulated as an emulsifiable concentrate (EC) or oil dispersion (OD) where it is dissolved in an organic solvent and thereby isolated from contact with water or as dry formulations such as a wettable powder (WP) or water dispersible granule (WG). Additives may also be included in these formulations to inhibit CQC-M hydrate formation or crystal growth upon dilution of the concentrates or dispersing of the granules into water for spray application as disclosed, for example, in US 2008/0058209 A1 or US 2008/0032890 A1.

Because of the increasing concern over use of organic solvents in agricultural formulations due to their cost, flammability, adverse health effects and contribution to environmental pollution, aqueous formulations have seen increasing use. The oil-in-water emulsion (EW) is one of the most common aqueous formulations used for many agricultural products, where droplets of oil stabilized by surfactant emulsifiers as a discrete phase are uniformly dispersed in water as a continuous phase. However, many stability challenges may exist with these formulations such as when the emulsion is physically unstable and phase separations occur or when oil soluble ingredients are incompatible with ingredients in the aqueous phase. CQC-M dissolved in the dispersed oil phase of an oil-in-water emulsion presents a particular challenge. Preventing contact of CQC-M with water is necessary to prevent CQC-M hydrate formation which will lead to crystal formation, Ostwald ripening and formulation instability. This invention provides a solution to the problem of making stable aqueous formulations containing CQC-M.

SUMMARY OF THE INVENTION

The present invention concerns a stable oil-in-water emulsion which comprises:
a) a discontinuous oil phase comprising, with respect to the oil-in-water emulsion, from about 200 g/L to about 800 g/L of oil solvent, from about 1 g/L to about 200 g/L of emulsion template solvent and from about 1 g/L to about 200 g/L of cloquintocet mexyl;
b) a continuous aqueous phase comprising, with respect to the oil-in-water emulsion, from about 200 g/L to about 700 g/L of water;
c) an emulsifying surfactant comprising, with respect to the oil-in-water emulsion, from about 1 g/L to about 100 g/L;
d) a polymeric dispersing surfactant comprising, with respect to the oil-in-water emulsion, from about 1 g/L to about 100 g/L; and
e) optionally, other inert formulation ingredients.

Another aspect of the present invention concerns an herbicidal composition which, in addition to the stable oil-in-water emulsion, contains an herbicide. Of particular interest are stable suspoemulsions in which an herbicide of low water and oil solubility is added as a dispersible active ingredient to the continuous aqueous phase of the oil-in-water emulsion.

DETAILED DESCRIPTION OF THE INVENTION

This invention provides an oil-in-water emulsion stabilized by a mixture of surfactants and solvents that hinder or prevent adverse interactions between cloquintocet mexyl dissolved in the discrete oil phase and the water of the continuous aqueous phase, which may lead to chemical or physical instabilities of the composition.

The oil phase of an oil-in-water emulsion contains components, such as solvents, adjuvants or other desirable ingredients that are essentially water immiscible. In a typical oil-in-water emulsion, the oil phase forms discrete droplets stabilized by emulsifiers that are suspended in a continuous aqueous phase. Interactions or reactions of the components in the oil phase with those in aqueous phase include, but are not limited to, hydrolysis of a component in the oil phase, or degradation of a component in the oil phase that is caused by the presence of other components in the aqueous phase, or crystal formation and growth (Ostwald ripening) in the aqueous phase of a component originally in the oil phase due to its relatively high water solubility or ability to form insoluble hydrates. CQC-M is an oil phase component that readily interacts with water to form an insoluble, crystalline hydrate that is subject to Ostwald ripening. These events may lead to formulations that are unstable and unsuitable for agricultural spray applications. The stable oil-in-water emulsion of the present invention prevents this from occurring.

The discontinuous oil phase of the present invention contains an oil solvent, an emulsion template solvent and CQC-M. It may optionally contain other oil soluble formulation ingredients or oil soluble active ingredients.

Oil solvents include, but are not limited to, one or more of petroleum fractions or hydrocarbons such as mineral oil, kerosene, paraffinic oils, mixed naphthalene and alkyl naphthalene fractions, aromatic solvents, particularly alkyl substituted benzenes such as xylene or propylbenzene fractions, and the like; dialkyl amides of fatty acids, particularly the dimethyl amides of fatty acids such as the dimethyl amide of caprylic acid; vegetable or seed oils such as soybean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable or seed oils; chlorinated aliphatic and aromatic hydrocarbons such as 1,1,1-trichloroethane and chlorobenzene; esters of glycol derivatives, such as the acetate ester of the n-butyl, ethyl, or methyl ether of diethyleneglycol and the acetate ester of the methyl ether of dipropyleneglycol; ketones such as isophorone and trimethylcyclohexanone (dihydroisophorone); and acetate ester products such as hexyl, or heptyl acetate, and the like.

Preferred oil solvents are petroleum fractions or hydrocarbons such as mineral oil, paraffinic oils and aromatic solvents like xylene, propylbenzene fractions, alkyl naphthalene fractions, and the like, vegetable or seed oils, esters of vegetable or seed oils and mixtures thereof.

The oil solvent comprises, with respect to the oil-in-water emulsion, from about 200 g/L to about 800 g/L, preferably from about 300 g/L to about 700 g/L.

The emulsion template solvent is defined as a water immiscible organic solvent that adds stability to the emulsion droplets and is well known to those skilled in the art. This solvent may be used alone or more commonly in combination with the oil solvents described previously. Typical emulsion template solvents are vegetable or seed oils such as soybean oil, rape seed oil, olive oil, castor oil, sunflower seed oil, coconut oil, corn oil, cotton seed oil, linseed oil, palm oil, peanut oil, safflower oil, sesame oil, tung oil and the like; esters of the above vegetable or seed oils; esters of monoalcohols or dihydric, trihydric, or other lower polyalcohols (4-6 hydroxy containing), such as 2-ethyl hexyl stearate, n-butyl oleate, isopropyl myristate, propylene glycol dioleate, di-octyl succinate, di-butyl adipate, di-octyl phthalate and the like; esters of mono, di and polycarboxylic acids and the like; small molecular weight homopolymers or co-polymers of the following, polyolefins such as polyallene, polybutadiene, polyisoprene, and poly(substituted butadienes) such as poly (2-t-butyl-1,3-butadiene), poly(2-chlorobutadiene), poly(2-chloromethyl butadiene), polyphenylacetylene, polyethylene, chlorinated polyethylene, polypropylene, polybutene, polyisobutene, polycyclopentylethylene and polycyclolhexylethylene, polyacrylates including polyalkylacrylates and polyarylacrylates, polymethacrylates including polyalkylmethacrylates and polyarylmethacrylates, polydisubstituted esters such as poly(di-n-butylitaconate), and poly (amylfumarate), polyvinylethers such as poly (butoxyethylene) and poly(benzyloxyethylene), poly(methyl isopropenyl ketone), polyvinyl chloride, polyvinyl acetate, polyvinyl carboxylate esters such as polyvinyl propionate, polyvinyl butyrate, polyvinyl caprylate, polyvinyl laurate, polyvinyl stearate, polyvinyl benzoate, polystyrene, poly-t-butyl styrene, poly (substituted styrene), poly(biphenyl ethylene), poly(1,3-cyclohexadiene), polycyclopentadiene and the like. Examples of suitable small molecular weight co-polymers are co-polymers of styrene, alkyl styrenes, isoprene, butenes, butadiene, acrylonitrile, alkyl acrylates, alkyl methacrylates, vinyl chloride, vinylidene chloride, vinyl esters of lower carboxylic acids and alpha, beta-ethylenically unsaturated carboxylic acids and esters thereof, including co-polymers containing three or more different monomer species therein.

Preferred emulsion template solvents are vegetable or seed oils such as soybean oil, rape seed oil, olive oil, castor oil, sunflower seed oil, coconut oil, corn oil, cotton seed oil, linseed oil, palm oil, peanut oil, safflower oil, sesame oil, tung oil and the like; simple esters of the above naturally derived oils; low molecular weight homopolymers (<5000) of the following, polyolefins such as polybutadiene, polyisoprene, and poly(substituted butadienes) such as poly(2-t-butyl-1,3-butadiene), polyethylene, chlorinated polyethylene, polypropylene, polybutene, polyisobutene, polycyclopentylethylene and polycyclolhexylethylene, polyacrylates including polyalkylacrylates and polyarylacrylates, polymethacrylates including polyalkylmethacrylates and polyarylmethacrylates, polydisubstituted esters such as poly(di-n-butylitaconate), and poly(amylfumarate), polyvinylethers such as poly (butoxyethylene) and poly(benzyloxyethylene), poly(methyl isopropenyl ketone), polyvinyl chloride, polyvinyl acetate, polyvinyl carboxylate esters such as polyvinyl propionate, polyvinyl butyrate, polyvinyl caprylate, polyvinyl laurate, polyvinyl stearate, polyvinyl benzoate, polystyrene, poly-t-butyl styrene, poly (substituted styrene), poly(biphenyl ethylene), poly(1,3-cyclohexadiene), polycyclopentadiene and the like; and low molecular weight (<5000) co-polymers of styrene, alkyl styrenes, isoprene, butenes, butadiene, acrylonitrile, alkyl acrylates, alkyl methacrylates, vinyl chloride, vinylidene chloride, vinyl esters of lower carboxylic acids and alpha, beta-ethylenically unsaturated carboxylic acids and esters thereof, including co-polymers containing three or more different monomer species and the like.

Most preferred emulsion template solvents are polyisobutene of low molecular weight (<1000) of which Indipol H-15 is a preferred example, vegetable or seed oils such as soybean oil, rape seed oil, olive oil, castor oil, sunflower seed oil, coconut oil, corn oil, cotton seed oil, linseed oil, palm oil, peanut oil, safflower oil, sesame oil, tung oil and the like; and $C_1$-$C_5$ esters of vegetable or seed oils and the like.

The emulsion template solvent comprises, with respect to the oil-in-water emulsion, from about 1 g/L to about 200 g/L, preferably from about 10 g/L to about 100 g/L.

The discontinuous oil phase of the present invention may optionally contain other oil soluble formulation ingredients and oil soluble active ingredients. The discontinuous oil phase may contain oil soluble dispersing or emulsifying surfactants, oil soluble adjuvants and oil miscible or soluble active ingredients. The active ingredients may include one or more herbicides, insecticides or fungicides, but are not limited to, esters of carboxylate, phosphate, or sulfate pesticides, including benzoic acid herbicides such as dicamba esters, phenoxyalkanoic acid herbicides such as 2,4-D, MCPA or 2,4-DB esters, aryloxyphenoxypropionic acid herbicides such as clodinafop, cyhalofop, fenoxaprop, fluazifop, haloxyfop and quizalofop esters, and pyridinecarboxylic acid herbicides such as aminopyralid, picloram, clopyralid, fluoroxypyr and triclopyr esters, and insecticides such as chlorpyrifos, chlorpyrifos-methyl, and fungicides such as dinocap, kresoxim-methyl, and the like.

The aqueous phase comprises water as the solvent medium, and optionally water soluble or water dispersible ingredients. Typically, water in the aqueous phase of the emulsion formulation is used to balance the final composition. Interactions or reactions of an ingredient in the aqueous phase with component(s) of the oil phase include, but are not limited to, crystal formation and growth due to Ostwald ripening of an oil phase component or an aqueous phase component, or chemical degradation of ingredients in either the oil phase or the aqueous phase. These degradations may be caused by the presence of one or more components in the oil-in-water emulsion and can lead to formulation instability. Migration of water into the oil phase and contact with CQC-M dissolved in the oil phase or migration of CQC-M into the water phase or to the oil-water interface can lead to CQC-M hydrate formation, crystal formation, Ostwald ripening and formulation instability or unsuitability for agricultural spray applications due to spray nozzle blockage.

The aqueous phase may optionally contain water soluble active ingredients such as salts of auxinic herbicides such as amine, alkylamine, dialkylamine, trialkylamine or metal salts of dicamba, phenoxyalkanoic acid herbicides such as 2,4-D, MCPA or 2,4-DB, pyridinecarboxylic acid herbicides such as fluoroxypyr, triclopyr, aminopyralid, clopyralid and picloram, and the like.

The aqueous phase comprises, with respect to the oil-in-water emulsion, from about 200 g/L to about 700 g/L, preferably from about 300 g/L to about 500 g/L.

CQC-M is a soluble component of the discrete oil phase and may comprise, with respect to the oil-in-water emulsion, from about 1 g/L to about 200 g/L, preferably from about 10 g/L to about 100 g/L.

A preferred oil phase composition that provides emulsion droplet stability will comprise the components of solvent, emulsion template solvent and CQC-M. Preferred ranges of these components are, on a relative weight ratio, from about 4 to 1 to about 14 to 1, and most preferably about 8 to 1, of the solvent and the emulsion template solvent, respectively, and from about 1 to 1 to about 1 to 3, and most preferably about 1 to 1, of the emulsion template solvent and CQC-M, respectively.

The surfactants used in this composition are comprised of one emulsifying surfactant and one polymeric dispersing surfactant.

Emulsifying surfactants that can be used are the following: (1) a mixture of 90% sorbitan trioleate with 20 ethylene oxide (PEG) units and 10% sorbitan trioleate, of which Emgard 2033-C is a preferred example; (2) a polyethylene glycol ether (10 units) of a $C_{11}$-$C_{13}$ mixture of alcohols, of which Synperonic 13/10 is a preferred example and (3) an n-butyl alcohol initiated EO-PO block copolymer, of which Atlas™ G-5000 (trademark of Uniqema) is a preferred example, and the like. Another example of such a polymeric surfactant is the commercial surfactant Termul™ 5429 (alcohol alkoxylate; trademark of Huntsman).

Preferred emulsifying surfactants are polyethylene glycol ethers (10 units) of a $C_{11}$-$C_{13}$ mixture of alcohols, a 90% sorbitan trioleate polyethoxylate (20 PEG units)—10% sorbitan trioleate mixture and an n-butyl alcohol initiated EO-PO block copolymer.

The emulsifying surfactant is present in an amount from about 1 g/L to about 100 g/L, preferably from about 1 g/L to about 50 g/L of the total composition.

Polymeric dispersing surfactants that can be used are the following: (1) a polyvinyl alcohol resin wherein the degree of hydrolysis is about 86-89%, of which Gohsenol GL03 and Gohsenol GL05 are preferred examples, (2) an ABA block copolymer having a hydrophilic portion of polyethylene oxide (PEG) and a hydrophobic portion of 12-hydroxystearic acid. A preferred example of such a polymeric surfactant is the commercial surfactant Atlox™ 4912 (trademark of Uniqema), having a molecular weight of about 5,000. Another example of such a polymeric dispersing surfactant is the commercial surfactant Termul™ 2510 (trademark of Huntsman), (3) a methyl methacrylate graft copolymer of which Atlox™ 4913 (trademark of Uniqema) is an example, (4) an alkyd polyethylene oxide resin of which Atlox™ 4914 is a preferred example, and the like.

Preferred polymeric dispersing surfactants are polyvinyl alcohols with about an 86-89% degree of hydrolysis of which Gohsenol GL03 and Gohsenol GL05 are preferred examples and a methyl methacrylate graft copolymer of which Atlox™ 4913 is an example.

The polymeric dispersing surfactant is present in an amount from about 1 g/L to about 100 g/L, preferably from about 1 g/L to about 50 g/L of the total composition.

In a typical procedure for preparing the oil-in-water emulsion of the present invention, the aqueous phase is prepared by mixing water with water soluble or water dispersible ingredients including, but not limited to, water soluble or water dispersible dispersing or emulsifying surfactants and optionally other inert ingredients such as thickener, pH buffer, wetting agent, antifreeze agent, antifoam agent, biocide, etc. The oil phase is prepared by mixing the oil-soluble dispersing or emulsifying surfactants with oil miscible or soluble ingredients, including but not limited to, oil solvents, emulsion template solvents and CQC-M. The final emulsion formulation is prepared by slowly adding the oil phase into the aqueous phase under high shear homogenization until the desired emulsion droplet size (0.1-5 μm) is achieved.

An example of a stable oil-in-water emulsion in which crystal growth due to Oswald ripening of CQC-M hydrate is retarded comprises:

a) a discontinuous oil phase comprising, with respect to the oil-in-water emulsion, from about 300 g/L to about 700 g/L of a petroleum aromatic solvent, from about 10 g/L to about 100 g/L of soybean oil and from about 10 g/L to about 100 g/L of cloquintocet mexyl;

b) a continuous aqueous phase comprising, with respect to the oil-in-water emulsion, from about 300 g/L to about 500 g/L of water;

c) an emulsifying surfactant comprising, with respect to the oil-in-water emulsion, from about 1 g/L to about 50 g/L of polyethylene glycol ethers of a $C_{11}$-$C_{13}$ mixture of alcohols;

d) a polymeric dispersing surfactant comprising, with respect to the oil-in-water emulsion, from about 1 g/L to about 50 g/L of a 86-89% hydrolyzed polyvinyl alcohol; and d) optionally, other inert formulation ingredients.

Another aspect of the present invention concerns a stable suspoemulsion in which an herbicide of low water and oil solubility is added as a dispersible active ingredient to the continuous aqueous phase of the oil-in-water emulsion.

Preferred aqueous dispersible active ingredients are herbicides that are water dispersible and have low oil and low water solubility and include, but are not limited to sulfonamides, sulfonylureas, arylpyridine carboxylic acids and esters, arylpyrimidine carboxylic acids and esters, imidazolinones and carbazones.

Herbicides which are especially suitable for dispersion in the aqueous phase are triasulfuron, tribenuron, metasulfuron, thifensulfuron, flupyrsulfuron, iodosulfuron, rimsulfuron, nicosulfuron, cinosulfuron, bensulfuron, trifloxysulfuron, foramsulphuron, mesosulphuron, sulphosulphuron, tritosulphuron and analogs, furthermore flumetsulam, metosulam, chloransulam, florasulam, diclosulam, penoxsulam, pyroxsulam and analogs, also imazethabenz, imazethapyr, imazaquin, imazamox and analogs, and flucarbazone, propoxycarbazone, amicarbazone and analogs, and compounds of the following generic structures disclosed in U.S. Pat. No. 7,314,849 B2 and U.S. Pat. No. 7,300,907 B2 wherein

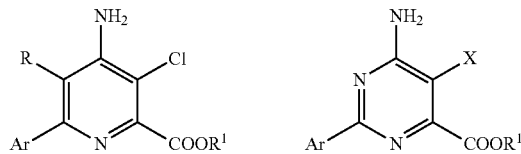

Ar is a polysubstituted phenyl group, R is H or halogen, $R^1$ is H or $C_1$-$C_8$ alkyl and X is halo. An especially suitable herbicide for dispersion in the aqueous phase is Compound A which has the following formula

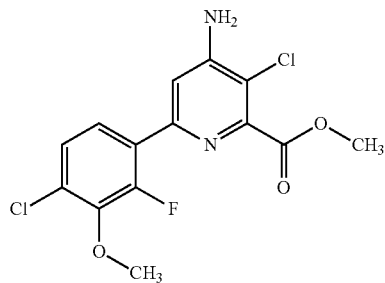 [SMILES: COC(=O)c1nc(-c2ccc(Cl)c(OC)c2F)cc(N)c1Cl]

For a suspoemulsion which may be further diluted at point of use, the aqueous dispersible herbicide may comprise, with respect to the suspoemulsion, from about 1 g/L to about 400 g/L, preferably from about 5 g/L to about 200 g/L, of the total composition. It is commonly known that this concentrated formulation may be diluted from 1 to 2000 fold at point of use depending on the agricultural practices.

In a typical procedure for preparing a suspoemulsion of the present invention, an aqueous phase containing a dispersed active ingredient is added to the oil-in-water emulsion with sufficient mixing. The aqueous phase is prepared by mixing water with a water-insoluble solid active (e.g. pyroxsulam), the solid material may be milled to a desirable size range (e.g. 0.1-10 μm, preferably 0.5-5 μm) and preferably pre-dispersed in a concentrated aqueous dispersion with the help of wetting agents and dispersants. There are many commercially available milling and dispersing processes and equipment that can be used for this purpose which are well known to those skilled in the art.

An example of a suspoemulsion in which crystal growth due to Oswald ripening of CQC-M hydrate or emulsion instability is retarded comprises:

a) a discontinuous oil phase comprising, with respect to the suspoemulsion, from about 300 g/L to about 700 g/L of a petroleum aromatic solvent, from about 10 g/L to about 100 g/L of polyisobutene of low molecular weight and from about 10 g/L to about 100 g/L of cloquintocet mexyl;

b) a continuous aqueous phase comprising, with respect to the suspoemulsion, from about 5 g/L to about 200 g/L of pyroxsulam, and any necessary wetting agents or dispersants, and from about 300 g/L to about 500 g/L of water;

c) an emulsifying surfactant comprising, with respect to the oil-in-water emulsion, from about 1 g/L to about 50 g/L of a polyethylene glycol ether of a $C_{11}$-$C_{13}$ mixture of alcohols;

d) a polymeric dispersing surfactant comprising, with respect to the oil-in-water emulsion, from about 1 g/L to about 50 g/L of a 86-89% hydrolyzed polyvinyl alcohol; and e) optionally, other inert formulation ingredients.

In addition to the compositions and uses set forth above, the present invention also embraces the composition and use of these oil-in-water emulsions and suspoemulsions in combination with one or more additional compatible ingredients. Other additional ingredients may include, for example, one or more other pesticides, dyes, and any other additional ingredients providing functional utility, such as, for example, stabilizers, fragrants, viscosity-modifying additives, suspension aids, dispersants, and freeze-point depressants.

The following example illustrates the present invention.

Example 1

Stability of Oil-in-Water Emulsions Containing Cloquintocet Mexyl

Five oil-in-water emulsions containing 5 wt percent cloquintocet mexyl, 4.5 wt percent propylene glycol, 2.5 wt percent of an emulsion template solvent, 37-42 wt percent of Aromatic 200 solvent and 2.5 wt percent each of the surfactants listed in Table 1 were prepared and tested for stability under accelerated storage conditions. Due to its tendency to form a hydrate in the presence of water, cloquintocet mexyl has a strong tendency to form crystals of the hydrate which undergo Oswald ripening causing crystal growth which eventually destabilizes or makes the formulation unsuitable for spray applications. The stability results are summarized in Table 1. All samples exhibited good stability after storage at 40° C. for twelve weeks as indicated by the good or very good quality of the emulsions, the absence of any crystal formation due to cloquintocet mexyl hydrate in any of the samples and the constant emulsion droplet size in each sample at that time point.

TABLE 1

Stability of Oil-in-Water Emulsions Containing Cloquintocet Mexyl
All samples contain: 5% cloquintocet mexyl, 37-42% Aromatic 200, 2.5% emulsion template
solvent, 4.5% propylene glycol, 2.5% of each surfactant, water and other common inert ingredients.

| | | | | | Samples After 12 Weeks @ 40° C. | | Samples @ 0 Weeks | |
| --- | --- | --- | --- | --- | --- | --- | --- | --- |
| Sample | Emulsion Template Solvent | Surfactant 1 | Surfactant 2 | Emulsion Quality | Crystal Growth | Emulsion Droplet Size, μM d (0.5) | Emulsion Droplet Size, μM d (0.9) | Emulsion Droplet Size, μM d (0.5) | Emulsion Droplet Size, μM d (0.9) |
| 1 | methyl soyate | Atlas G5000 | Gohsenol GL03 | 4 | no | 0.95 | 1.44 | 0.93 | 1.4 |
| 2 | Indopol H15 | Synperonic 1310 | Atlox 4913 | 4 | no | 0.86 | 1.34 | 0.84 | 1.31 |
| 3 | Indopol H-15 | Synperonic 1310 | Gohsenol GL03 | 5 | no | 0.4 | 0.72 | 0.39 | 0.7 |
| 4 | soybean oil | Synperonic 1310 | Atlox 4913 | 4 | no | 0.78 | 1.23 | 0.78 | 1.23 |
| 5 | soybean oil | Synperonic 1310 | Gohsenol GL03 | 5 | no | 0.37 | 0.64 | 0.37 | 0.65 |

Crystals Growth: no = no crystals observed upon examination under a microscope
Emulsion Quality: 5 = very good, 4 = good, 3 = weak, 2 = poor, 1 = no emulsion Example 2

Stability of a Suspoemulsion Containing Cloquintocet Mexyl

The oil-in-water emulsion of cloquintocet-mexyl (82.8 g, Sample 3 in Table 1) was blended with a 40 weight percent on an acid equivalent basis (wt % ae) of an aqueous suspension concentrate of Compound A (10.3 g) and a 45 wt % aqueous suspension concentrate of florasulam (6.9 g) with mild agitation. The resulting suspoemulsion demonstrated good stability after storage at 40° C. for 8 weeks. Neither crystal growth nor phase separation was observed in the suspoemulsion.

Example 3

Stability of a Suspoemulsion Containing Cloquintocet Mexyl

An oil-in-water emulsion was prepared with cloquintocet-mexyl (1.0 wt %), Agnique ME 18S-U (45.0 wt %), Indopol H-15 (2.5 wt %), Gohsenol GL03 (2.5 wt %), Synperonic 1310 (2.5 wt %), propylene glycol (4.5 wt %), and water (40.50 wt %). The suspoemulsion was produced by blending a 40 wt % ae aqueous suspension concentrate of Compound A (1.8 g), a 45 wt % aqueous suspension concentrate of florasulam (1.2 g) and the 1 wt % oil-in-water emulsion of cloquintocet-mexyl (97.0 g) with mild agitation. The resulting suspoemulsion demonstrated good stability after storage at 40° C. for 6 weeks. Neither crystal growth nor phase separation was observed in the suspoemulsion.

Example 4

Preparation of a Suspoemulsion Containing Cloquintocet Mexyl, Compound A and Aminopyralid Potassium The oil-in-water emulsion of cloquintocet-mexyl (72.0 g, Sample 3 in Table 1) was blended with a 40 wt % ae aqueous suspension concentrate of Compound A (9.0 g) and a 15.8 wt % (on an acid equivalent basis) aqueous solution of Aminopyralid potassium salt (19 g) with mild agitation to form the suspoemulsion.

What is claimed is:

1. A stable oil-in-water emulsion which comprises:
   a) a discontinuous oil phase comprising, with respect to the oil-in-water emulsion, from about 200 g/L to about 800 g/L of oil solvent, from about 1 g/L to about 200 g/L of emulsion template solvent and from about 1 g/L to about 200 g/L of cloquintocet mexyl;
   b) a continuous aqueous phase comprising, with respect to the oil-in-water emulsion, from about 200 g/L to about 700 g/L of water;
   c) an emulsifying surfactant comprising, with respect to the oil-in-water emulsion, from about 1 g/L to about 100 g/L;
   d) a polymeric dispersing surfactant comprising, with respect to the oil-in-water emulsion, from about 1 g/L to about 100 g/L; and
   e) optionally, other inert formulation ingredients;
   wherein the oil-in-water emulsion is stable for at least 6 weeks at 40° C. as indicated by the absence of crystals due to cloquintocet-mexyl hydrate formation as determined by examination with a microscope using polarized light.

2. An herbicidal composition which comprises, in addition to the stable oil-in-water emulsion of claim 1, an herbicide.

3. The herbicidal composition of claim 2 which comprises a stable suspoemulsion in which an herbicide of low water and oil solubility is added as a dispersible active ingredient to the continuous aqueous phase of the oil-in-water emulsion of claim 1.

4. The stable suspoemulsion of claim 3 wherein the herbicide is pyroxsulam.

5. The stable suspoemulsion of claim 3 wherein the herbicide is an arylpyridine carboxylic acid or ester of the formula

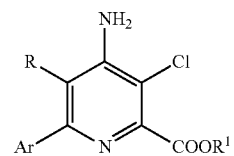

wherein Ar is a polysubstituted phenyl group, R is H or halogen and $R^1$ is H or $C_1$-$C_8$ alkyl.

6. The composition of claim 5 wherein the arylpyridine carboxylic acid or ester has the formula

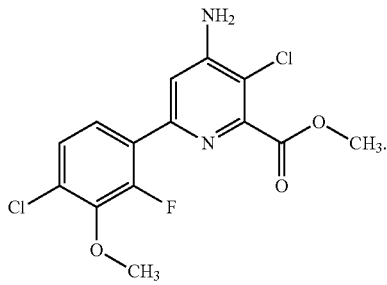 [SMILES: COC(=O)c1nc(-c2ccc(Cl)c(OC)c2F)cc(N)c1Cl]

7. The composition of claim 2 wherein the herbicide is triasulfuron, tribenuron, metasulfuron, thifensulfuron, flupyrsulfuron, iodosulfuron, rimsulfuron, nicosulfuron, cinosulfuron, bensulfuron, trifloxysulfuron, foramsulphuron, mesosulphuron, sulphosulphuron, tritosulphuron and analogs, furthermore flumetsulam, metosulam, chloransulam, florasulam, diclosulam, penoxsulam, pyroxsulam, imazethabenz, imazethapyr, imazaquin, imazamox, flucarbazone, propoxycarbazone, amicarbazone, or a compound of the formula I or II:

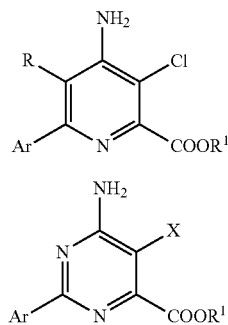

wherein Ar is a polysubstituted phenyl group, R is H or halogen, $R^1$ is H or $C_1$-$C_8$ alkyl and X is halo; or a carboxylic acid, ester, or salt thereof.

8. The composition of claim 2, wherein the emulsion template solvent is a polyisobutylene having a molecular weight of less than 1000, vegetable oil or an ester thereof, or seed oil or an ester thereof.

9. The composition of claim 2, wherein the emulsion template solvent is a polyisobutene having a molecular weight of less than 1000, methyl soyate, or soybean oil.

10. The composition of claim 2, wherein the discontinuous oil phase comprises, with respect to the oil-in-water emulsion, from about 10 g/L to about 100 g/L of emulsion template solvent.

11. The composition of claim 2, wherein the discontinuous oil phase comprises, with respect to the oil-in-water emulsion, from about 10 g/L to about 100 g/L of cloquintocet mexyl.

12. The composition of claim 2, wherein the emulsifying surfactant is a polyethylene glycol ether of a $C_{11}$-$C_{13}$ mixture of alcohols or an n-butyl alcohol initiated EO-PO block copolymer.

13. The composition of claim 2, wherein the emulsifying surfactant is present, with respect to the oil-in-water emulsion, in an amount from about 1 g/L to about 50 g/L.

14. The composition of claim 2, wherein the polymeric dispersing surfactant is a polyvinyl alcohol resin having a degree of hydrolysis of about 86 to 69 percent or a methyl methacrylate graft copolymer.

15. The composition of claim 2, wherein the polymeric dispersing surfactant is present, with respect to the oil-in-water emulsion, in an amount from about 1 g/L to about 50 g/L.

16. The composition of claim 3, wherein the emulsion template solvent is polybutene.

17. The composition of claim 1, wherein
(i) the emulsifying surfactant is
  (a) a mixture 90% sorbitan trioleate with 20 ethylene oxide units and 10% sorbitan trioleate,
  (b) a polyethylene glycol ether of a $C_{11}$-$C_{13}$ mixture of alcohols, or
  (c) an n-butyl alcohol initiated EO-PO block copolymer;
(ii) the polymeric dispersing surfactant is:
  (a) a polyvinyl alcohol resin having a degree of hydrolysis of about 86 to 89 percent;
  (b) an ABA block copolymer having a hydrophilic portion of polyethylene oxide and a hydrophobic portion of 12-hydroxystearic acid;
  (c) a methyl methacrylate graft copolymer; or
  (d) an alkyd polyethylene oxide resin.

18. The composition of claim 1, wherein the oil-in-water emulsion comprises about 10 to about 100 g/L of an emulsion template solvent and about 10 to about 100 g/L of cloquintocet mexyl.

19. The composition of claim 18, wherein the composition does not contain any one of an ABA block copolymer having a hydrophilic portion of polyethylene oxide and a hydrophobic portion of 12-hydroxystearic acid, 2-(4-(3-chloro-5-fluoro-2-pyridyloxy)-phenoxy)-propionic acid propargyl ester, pyrasulfotole and pyroxsulam.

20. The oil-in-water emulsion of claim 1, wherein the oil-in water emulsion is stable for at least 12 weeks.

21. A stable oil-in-water emulsion which consists essentially of:
a) a discontinuous oil phase comprising, with respect to the oil-in-water emulsion, from about 200 g/L to about 800 g/L of oil solvent, from about 1 g/L to about 200 g/L of emulsion template solvent and from about 1 g/L to about 200 g/L of cloquintocet mexyl;
b) a continuous aqueous phase comprising, with respect to the oil-in-water emulsion, from about 200 g/L to about 700 g/L of water;
c) an emulsifying surfactant comprising, with respect to the oil-in-water emulsion, from about 1 g/L to about 100 g/L; and
d) a polymeric dispersing surfactant comprising, with respect to the oil-in-water emulsion, from about 1 g/L to about 100 g/L;
wherein the oil-in-water emulsion is stable for at least 6 weeks at 40° C. as indicated by the absence of crystals due to cloquintocet-mexyl hydrate formation as determined by examination with a microscope using polarized.

22. A stable oil-in-water emulsion which comprises:
a) a discontinuous oil phase comprising, with respect to the oil-in-water emulsion, from about 200 g/L to about 800 g/L of oil solvent, from about 1 g/L to about 200 g/L of emulsion template solvent and from about 1 g/L to about 200 g/L of cloquintocet mexyl;
b) a continuous aqueous phase comprising, with respect to the oil-in-water emulsion, from about 200 g/L to about 700 g/L of water;

c) an emulsifying surfactant comprising, with respect to the oil-in-water emulsion, from about 1 g/L to about 100 g/L, wherein the emulsifying surfactant
   (i) a mixture 90% sorbitan trioleate with 20 ethylene oxide units and 10% sorbitan trioleate,
   (ii) a polyethylene glycol ether of a $C_{11}$-$C_{13}$ mixture of alcohols, or
   (iii) an n-butyl alcohol initiated EO-PO block copolymer;
d) a polymeric dispersing surfactant comprising, with respect to the oil-in-water emulsion, from about 1 g/L to about 100 g/L, wherein the polymeric dispersing surfactant is:
   (i) a polyvinyl alcohol resin having a degree of hydrolysis of about 86 to 89 percent;
   (ii) an ABA block copolymer having a hydrophilic portion of polyethylene oxide and a hydrophobic portion of 12-hydroxystearic acid;
   (iii) a methyl methacrylate graft copolymer; or
   (iv) an alkyd polyethylene oxide resin;
e) propylene glycol; and
f) optionally, other inert formulation ingredients.

* * * * *